United States Patent [19]

Umemura

[11] 4,001,334

[45] Jan. 4, 1977

[54] RACEMIZATION OF OPTICALLY ACTIVE ALLETHROLONE

[75] Inventor: Takeaki Umemura, Takarazuka, Japan

[73] Assignee: Sumitomo Chemical Company, Limited, Osaka, Japan

[22] Filed: July 21, 1975

[21] Appl. No.: 597,813

[30] Foreign Application Priority Data

Aug. 12, 1974 Japan .............................. 49-92653

[52] U.S. Cl. ...................... 260/586 R; 260/566 A; 260/DIG. 7
[51] Int. Cl.$^2$ ................... C07C 45/00; C07B 20/00
[58] Field of Search ............................... 260/586 R

[56] References Cited

UNITED STATES PATENTS 2,891,888   6/1959   Guest et al. .................. 260/586 R

OTHER PUBLICATIONS

Ebel, "Stereo Chemistry of Carbon Compounds", pp. 31–47 (1962).

*Primary Examiner*—Norman Morgenstern
*Attorney, Agent, or Firm*—Wenderoth, Lind & Ponack

[57] ABSTRACT

The present invention provides a process for preparing racemic allethrolone which comprises reacting (−) allethrolone with hydroxylamine to form the corresponding allethrolone.oxime and then hydrolyzing the oxime in water or a mixture of water and an organic solvent miscible with water in the presence of an acid.

4 Claims, No Drawings

RACEMIZATION OF OPTICALLY ACTIVE ALLETHROLONE

The present invention relates to a process for preparing racemic allethrolone from the optically active allethrolone.

Allethrolone is an alcohol moiety of cyclopropanecarboxylic acid esters which are the active ingredients of pyrethroid insecticides, for example allethrin which is useful as a low-toxic insecticide, and exists in two optical isomers, i.e., the (+) and (−) isomers. Of the two isomers, a pyrethroid insecticide having in its alcohol moiety the (+) isomer is much superior to that of the other isomer in efficacy.

It is well known from Belgian Pat. No. 793,190 (1971) and Japanese Open Pat. Publication No. 75,545/1973 that (±) allethrolone can be resolved into the two optically active isomers by treating (±) allethrolone half-esters as an intermediate, for example (±) allethrolone acid succinate and (±) allethrolone acid phthalate, with optically active bases such as ephedrine and α-phenyl-β-(p-tolyl)-ethylamine.

But, the resolution by this well-known method not only produces (+) allethrolone which is useful as the alcohol moiety, but also produces (−) allethrolone as a by-product, of which ester is much inferior in insecticidal activity, and so it has little industrial value. Therefore, re-conversion of the useless (−) allethrolone to valuable (+) allethrolone or (±) allethrolone has a great industrial significance.

There has been a known method, in the literature (La Forge et al., J. Org. Chem., 19, 457 (1954)), relating to the process for obtaining optically active allethrolone in which the optically active allethrolone was prepared by hydrolyzing optically active allethrolone.semicarbazone under restricted acidic conditions. In the literature there was only a simple disclosure that longer treatment is to be avoided because of a tendency toward racemization, but there was no description about detailed points.

The present inventor followed this known method, reacted optically active allethrolone with semicarbazide to form optically active allethrolone.semicarbazone and then hydrolyzed the semicarbazone under acidic conditions. According to this process, racemic allethrolone was obtained, but the yield was low, and therefore the known process was not an industrially advantageous racemization process. Further, the present inventor reacted optically active allethrolone with hydrazine to form optically active allethrolone hydrazone and then hydrolyzed the hydrazone under acidic conditions. According to this process only partially racemized allethrolone was obtained in low yield, and so the process could not be recognized possibly to be an industrially advantageous process.

In order to overcome the said defects in the conventional processes, the present inventor effected various studies, and found that almost completely racemized allethrolone could be obtained in a high yield by reacting optically active allethrolone with hydroxylamine to form optically active allethrolone.oxime and then hydrolyzing the oxime in water or a mixture of water and an organic solvent miscible with water in the presence of an acid.

One object of the present invention is to provide a commercially advantageous racemization process of producing racemic allethrolone from (−) allethrolone.

Other objects of the present invention are apparent from the following description.

In order to accomplish these objects, the present invention provides a process for obtaining racemic allethrolone which comprises reacting (−) allethrolone with hydroxylamine to form the corresponding allethrolone.oxime and then hydrolyzing the oxime in water or a mixture of water and an organic solvent miscible with water in the presence of an acid.

In carrying out the process of the present invention, in the first reaction step, optically active allethrolone.oxime can be obtained by reacting optically active allethrolone with hydroxylamine which is freed from its hydrochloride or sulfate thereof according to an ordinary method (e.g. by adding a suitable basic agent such as pyridine, triethylamine, sodium acetate and sodium carbonate thereto).

In the second reaction step, water or a mixture of water and an organic solvent miscible with water is used in the presence of a mineral acid or an organic acid in a process of hydrolyzing optically active allethrolone oxime. Acids used in the present invention include hydrochloric acid, sulfuric acid, acetic acid, oxalic acid, pyruvic acid, levulinic acid, trifluoroacetic acid and the like, and a mixture thereof. Solvents used in the second step include water and a mixture of water and an organic solvent miscible with water (e.g. acetone, acetylacetone, dioxane, tetrahydrofuran and a mixture thereof).

The reaction temperature in the second step can be varied from under cooling to the boiling point of the solvent used (e.g. the boiling point of the organic solvent, a mixture of water and the organic solvent or water), preferably from 0° C. to 200° C., but not limitative thereto. k The present invention will be illustrated with reference to the following examples, which are only given for the purpose of illustration and not be interpreted as limiting thereto.

EXAMPLE 1

Step 1

In 100 ml. of aqueous ethanol (70%) were dissolved 8.34 g. (0.12 mole) of hydroxylamine hydrochloride, and then 9.49 g. (0.12 mole) of pyridine and 15.2 g. (0.1 mole) of (−) allethrolone ($[\alpha]_D^{23} = -9.13°$ (chloroform)) were added thereto, and the resulting mixture was refluxed for an hour.

After the reaction was completed ethanol was distilled off under reduced pressure, and the residue was extracted with ether. The ether extracts were dried over anhydrous sodium sulfate, filtered, and then ether was evaporated and cooled.

13.7 g. of (−) allethrolone.oxime were obtained as crystals.

(Yield: 82.0%, Melting Point: 109° – 112° C., $[\alpha]_D^{22} = +44.0°$ )).

| Elementary Analysis Calculated (%) (as $C_9H_{13}NO_2$) | Found (%) |
|---|---|
| C: 64.65 | 64.83 |
| H: 7.84 | 7.62 |
| N: 8.38 | 8.53 |

As far as it has been known, this oxime has not been disclosed in any literature.

Step 2

1. 5.01 g. (0.03 mole) of (—) allethrolone.oxime thus obtained were refluxed in 60 ml. of 5% aqueous sulfuric acid for 3 hours. After the reaction was completed, the reaction solution was cooled, saturated with sodium chloride and then extracted with ether. Ether extracts were washed with saturated sodium chloride solution, dried over anhydrous sodium sulfate, the ether was evaporated to obtain 2.84 g. of racemic allethrolone. (Yield: 62.3%, Boiling Point: 105° – 107° C./0.4 mmHg, $[\alpha]_D^{23} = \pm 0°$ (chloroform)).

2. 5.01 g. (0.03 mole) of (—) allethrolone.oxime obtained according to Step 1 were refluxed in 60 ml. of 5% aqueous sulfuric acid containing 17.4 g. of acetone for 3 hours. After the reaction was completed, the reaction solution was cooled and treated with the same manner as mentioned in Step 2 - (1) to obtain 4.56 g. of racemic allethrolone.
(Yield: 79.6%, Boiling Point: 105°– 107° C./0.4 mmhg, $[\alpha]_D^{23} = \pm 0°$ (ethanol)).

EXAMPLE 2

In 30 ml. of water were dissolved 8.34 g. (0.12 mole) of hydroxylamine hydrochloride, and then 9.49 g. (0.12 mole) of pyridine and 15.2 g. (0.1 mole) of (—) allethrolone ($[\alpha]_D^{23} = -9.13°$ (chloroform)) in 70 ml. of ethanol were added to the resulting solution and refluxed for about an hour. After the reaction was completed, the ethanol was distilled off under reduced pressure. To the residue 58.0 g. of acetone and 160 ml. of 5% aqueous sulfuric acid were added and refluxed for 6 hours. The reaction solution was cooled and treated with the same manner as mentioned in Example 1, Step 2 - (1) to obtain 12.9 g. of racemic allethrolone. (Yield: 84.9%, Boiling Point: 104° – 107° C./0.4 mmHg, $[\alpha]_D^{21.5} = -0.12°$ (chloroform)).

What we claim is:

1. A process for preparing racemic allethrolone which comprises reacting (—) allethrolone with hydroxylamine to form the corresponding allethrolone oxime and then hydrolyzing the oxide to racemic allethrolone by contacting it with water or a mixture of water and an organic solvent miscible with water at a temperature between 0° C and 200° C in the presence of an acid, wherein said organic solvent is a member selected from the group consisting of acetone, acetylacetone, dioxane, tetrahydrofuran and mixtures thereof and said acid is a member selected from the group consisting of hydrochloric acid, sulfuric acid, acetic acid, oxalic acid, pyruvic acid, levulinic acid, trifluoroacetic acid and mixtures thereof, said acid being used in amounts sufficient to hydrolyze the allethrolone.oxime to the objective racemic allethrolone.

2. The process according to claim 1, wherein the hydrolyzing reaction is carried out in water or a mixture of water and acetone.

3. The process according to claim 1, wherein the acid is sulfuric acid.

4. A process according to claim 3 wherein a 5% aqueous solution of sulfuric acid is used.

* * * * *